United States Patent [19]

Cheney et al.

[11] Patent Number: 5,390,110
[45] Date of Patent: Feb. 14, 1995

[54] LAYER STRIPPING PROCESS FOR IMPEDANCE IMAGING

[75] Inventors: Margaret Cheney, Troy; David Isaacson, Latham, both of N.Y.; Erkki Somersalo, Helsinki, Finland; Eli L. Isaacson, Laramie, Wyo.

[73] Assignee: Rensselaer Polytechnic Institute, Troy, N.Y.

[21] Appl. No.: 727,075

[22] Filed: Jul. 9, 1991

[51] Int. Cl.[6] .................. G06F 15/42; A61B 5/05
[52] U.S. Cl. .................. 364/413.13; 128/734
[58] Field of Search ........... 64/413.01, 413.02, 413.13, 64/413.14; 128/734

[56] References Cited

U.S. PATENT DOCUMENTS

| 4,291,708 | 9/1981 | Frei et al. ........................ 128/734 |
| 4,486,835 | 12/1984 | Bai et al. ...................... 128/734 X |
| 4,539,640 | 9/1985 | Fry et al. ...................... 128/734 X |
| 4,794,934 | 1/1989 | Motoyama et al. ................ 128/734 |
| 4,920,490 | 4/1990 | Isaacson ........................ 364/413.13 |

OTHER PUBLICATIONS

*IEEE Transactions on Geoscience and Remote Sensing*, vol. GE-25, No. 5, Sep. 1987, Yagle, "A Layer Stripping Fast Algorithm for the Two-Dimensional Direct Current Inverse Resistivity Problem", pp. 558–563.

*Inverse Problems*, vol. 4, 1988, Cheney et al., "Three dimensional inverse scattering; layer-stripping formulae and ill-posedness results", pp. 625–642.

*Inverse Problems*, vol. 4, 1988, Cheney et al., "Three-dimensional inverse scattering for the wave equation; weak scattering approximations with error estimates", pp. 435–447.

*IEEE Proceedings*, vol. 132, No. 7, Nov. 1985, Seager et al., "Full-wave computed tomography Part 4: Low-frequency electric current CT", pp. 455–466.

*IEEE Proceedeings*, vol. 131, No. 8, Nov. 1984, Seager et al., "Full-wave computed tomography Part 2: Resolution limits", pp. 16–22.

Lytle et al., "An Impedance Camera: A System for Determining the Spatial Variation of Electrical Conductivity", Lawrence Livermore Report UCR-L-S2413, 1978.

*IEEE Transactions on Biomedical Engineering*, vol. BME-25, No. 3, May 1978, Henderson et al., "An Impedance Camera for Spatially Specific Measurements of the Thorax", pp. 250–255.

*IEEE Transaction on Medical Imaging*, vol. MI-5, No. 2, Jun. 1986, Isaacson, "Distinguishability of Conductivities by Electric Current Computed Tomography", pp. 91–95.

*IEEE Transactions on Biomedical Engineering*, vol. BME-32, No. 3, Mar. 1985, Murai et al., "Electrical Impedance Computed Tomography Based on a Finite Element Model", pp. 177–184.

*IEEE Transactions on Biomedical Engineering*, vol. BME-27, No. 7, Jul. 1980, Bates et al., "A Limitation on Systems for Imaging Electrical Conductivity Distributions", pp. 418–420.

*IEEE Transactions on Nuclear Science*, vol. NS-26, No. 2, Apr. 1979, Price, "Electrical Impedance Computed Tomography (ICT): A New CT Imaging Technique", pp. 2736–2739.

i SPIE, vol. 206, 1979, Price, "Imaging of the electrical conductivity and premittivity inside a patient: a new computed tomography (CT) technique", pp. 115–119.

*Primary Examiner*—David M. Huntley
*Attorney, Agent, or Firm*—Notaro & Michalos

[57] ABSTRACT

A method for the impedance imaging of a three-dimensional body utilizes electrodes. On the outer surface of the body which receive a set of current patterns. The resulting voltage patterns are measured at the outer boundary of the body. Synthesized resulting patterns are then calculated for inner boundaries of the body, each at a selected incremental distance inwardly of the outer boundary. The synthesis step is repeated for successive inner boundaries until the center of the body is reached. The measured and synthesized patterns are utilized to calculate or otherwise find various medium properties in the body, such as the electric conductivity and electric permittivity for the body. These impedance characteristics based on the measured and synthesized patterns are used to produce an image of the body.

6 Claims, 5 Drawing Sheets

LAYER STRIPPING PROCESS FOR IMPEDANCE IMAGING

STATEMENT OF GOVERNMENT INTEREST

This invention was made in part with Government support under National Science Foundation Grant No. EET-8706340, National Institutes of Health Research Grants GM-39388 and GM-42935, and the Office of Naval Research Grant N-00014-89-J-1129. The Government has certain rights in this invention.

FIELD AND BACKGROUND OF THE INVENTION

The present invention relates in general to electrical impedance tomography, and in particular to a new and useful method and apparatus for making electrical impedance images which are significantly faster and more accurate than any previously known method, by first finding the impedance on the boundary of a body to be imaged, using this information to figuratively strip away the outer layer of the body, and thereafter repeating the process in a layer-by-layer manner until information on the full depth of the body is obtained.

An apparatus for practicing electric current computed tomography (ECCT) comprising 32 electrodes and a plurality of current generators is disclosed in U.S. Pat. No. 4,920,490 granted to one of the co-inventors of the present invention. U.S. Pat. No. 4,920,490 is incorporated here by reference and discloses a means for distinguishing one conductivity from another in the body to be imaged.

ECCT is used to determine electrical impedance distribution within a body from electrical measurements made on the surface of the body. It has a wide range of possible applications in medical imaging, geology and mineral exploration, in the nondestructive evaluation of materials, and in the control of manufacturing processes.

There is previous literature on layer-stripping methods for reconstructing internal medium parameters of a body from measurements made on the boundary or outer surface of the body. However, this previous literature generally deals with hyperbolic problems, that problems involving time and wave propagation. These methods are based on the idea of splitting the waves into upward-propagating and downward-propagating components.

In contrast, the process of the present invention deals with an elliptic problem, i.e., a solid-state problem. No wave splitting is involved.

In addition, nearly all the previous literature deals with problems that are essentially one-dimensional, which the medium parameters depend on only one variable One paper that does deal with a multidimensional elliptic problem is M. Cheney and G. Kristensson, "Three-dimensional inverse scattering: layer-stripping formulae and ill-posedness results," in *Inverse Problems* 4 (1988) 625–642. This paper considers a time-independent wave equation, which is not the correct mathematical model for the impedance imaging problem.

A second related paper is one that does attempt to solve the multidimensional impedance imaging problem: A. E. Yagle, "A layer stripping fast algorithm for two-dimensional direct current inverse resistivity problem", in *IEEE Trans. Geoscience and Remote Sensing* GE-25 (1987) 558–563. This paper uses a method that involves analytic continuation, a process that is so unstable that the method described would not work in practice. Moreover, it uses a method that does not work if the medium varies in all dimensions, i.e., for a two-dimensional problem the medium must be only one-dimensional, and for a three-dimensional problem the medium can be only two-dimensional. In contrast, the process of the present invention applies to media that are fully two- or three-dimensional.

Finally, most of the previous work is purely mathematical. In contrast, the present invention is a process that has been reduced to practice.

SUMMARY OF THE INVENTION

An object of the present invention is to provide a technique for imaging the full depth of a body using information obtained by surface electrodes on outer boundary of the body.

Using for example, the apparatus of U.S. Pat. No. 4,920,490 currents (or voltages) are applied to the boundary and the resulting voltages (or currents) are measured. The data thus provided is subjected to a subsurface data synthesis technique of the present invention to produce information about the electrical conductivity and electrical permittivity in the interior of the body. This information can thereafter be used to generate an image of the interior of the body.

The subsurface data synthesis technique of the present invention, in effect, strips away one outermost layer at a time from the outer surface or boundary to the center of the body to produce the image information, layer by layer.

By applying current densities with very rapid spatial variation to the surface of the body, the corresponding currents do not penetrate very deeply into the body but rather are affected mainly by the conductivity near the boundary. Because of this, the voltage measurements can be used to find the conductivity in a thin layer at the boundary.

In this disclosure, the case for a two-dimensional disk is explained in detail with each layer having a radius which is reduced, increment by increment, to the center of the disk. The invention can be generalized, however, to any geometry and for a two, three or even higher dimensional problem while applying the principles of the present invention.

In addition, the invention applies to obtaining images of either the electrical conductivity or the electrical permittivity or both. In this disclosure, only the conductivity is considered for simplicity.

The present invention can also be used in the case in which one applies a voltage pattern and measures the charges that build up at the electrodes (see, C. G. Xie, A. Plaskowski, and M. S. Beck, "8-electrode capacitance system for two-component flow identification", Parts 1 and 2, IEE Proc. 136, *Pt. A* (1989) 173–190).

Similarly, it can be used in the case in which one applies specified patterns of charges and measures the corresponding voltage patterns.

Accordingly, a further object of the present invention is to provide a method of creating a conductivity image of the volume of a body having an outer boundary, comprising: (a) applying a set of current or voltage patterns to the outer boundary of the body; (b) measuring the actual resulting and respective voltage or current patterns at the outer boundary; (c) finding this conductivity at the outer boundary of the body based on the resulting pattern; (d) synthesizing a set of calculated resulting patterns for a first inner boundary of the body which is at a selected incremental distance inward of the outer boundary; (e) finding the conductivity at the inner boundary of the body based on the calculated resulting pattern; (f) synthesizing a set of calculated resulting patterns for a second inner boundary of the body which is at the selected incremental distance inward of the first inner boundary; (g) repeating steps (e) and (f) for additional inner boundaries until the selected incremental distance inward reaches a selected depth in the body; and (h) using the conductivity thus obtained to form an image of the body from the outer boundary to the selected depth.

When a naive version of the method-of-the present invention is applied in practice, wild oscillations are sometimes produced. To solve this problem, another object of the present invention is to provide such a method wherein the calculated resulting patterns are subjected to regularization. Regularization can be achieved in a variety of ways. One of these involves writing the applied current patterns in terms of their Fourier series, i.e., writing them as sums of sines and cosines. Regularization is achieved by selectively dropping modes from each Fourier series on the basis of the layer currently being analyzed. Terms which are least relevant for the particular layer being processed are dropped in this way, so that the remaining modes or terms give information which is most relevant for the layer in question. The current patterns which oscillate most rapidly in space, are the patterns with the higher Fourier modes that contain least information about the particular layer being analyzed. This mode is the one that is dropped. This is based on the concept used in obtaining the best current pattern disclosed in U.S. Pat No. 4,920,490 where the best patterns are selected to contain most information about the heart of the body which is furthest from the electrodes.

Another way to regularize is by using a minimization procedure to synthesize the measurements at the next layer. Thus one would first find the impedance distribution of a layer. One would then think of applying a set of current patterns to the inner surface, and guess the resulting voltage patterns. From knowledge of this synthesized data on the subsurface and the outer impedance distribution, the corresponding measurements on the outer surface can be calculated. The patterns on the inner surface would be adjusted so that the calculated ones on the outer surface agreed with the already known ones. (See, for example, P. Colli Franzone, "Il progleme inverso dell'eletrrocardiografia", Boll. U.M.I. 15-A (1978) 30–51; also P. Colli Franzone, L. Guerri, B. Taccardi and C. Viganotti, "The direct and inverse potential problems in electrocardiology. Numerical aspects and application to data collected in isolated dog heart experiments", Pub. 22, laboratorio di Analisi Numerica Del Consiglio Nationale delle Richerche, Pavia, 1979).

Another way to regularize is by adding smoothing terms in the appropriate equations.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

The impedance imaging problem can be formulated mathematically as follows. For simplicity only the electrical conductivity, which is denote by $\sigma$, rather than the full electrical impedance, is considered. The electric potential u satisfies the boundary value problem $$\nabla \cdot (\sigma \nabla u) = 0 \text{ inside the body } \Omega \qquad (1.1)$$

$$\sigma \frac{\partial u}{\partial \nu} = j \text{ on the surface of } \partial \Omega. \qquad (1.2)$$

For simplicity, we will assume throughout that the body $\Omega$ is a disk of radius r.

We assume that we may make any boundary measurements we like. This means that we may specify any j and measure the corresponding u on the boundary. Equivalently, we assume that we can obtain from measurements the map R that takes j to the boundary values of u. We call this map the resistive map. From knowledge of the map R, we would like to find $\sigma$.

In the following, we need to extend the definition of R to all r:

$$R(r)\left(\sigma(r,\Theta)\frac{\partial u(r,\Theta)}{\partial r}\right) = u(r,\Theta). \qquad (1.3)$$

Most of the reconstruction methods that have actually made images have been of two kinds, those based on linearization and those based on optimization. Methods based on linearization can yield useful images, but the reconstructed values of the conductivity are accurate only in special cases. Optimization methods can be more accurate but they tend to be computationally intensive and can have difficulties with extraneous local minima.

The layer-stripping method of the present invention works by first finding the conductivity in a thin layer near the boundary, stripping away this layer, and then repeating the process. More specifically, the steps are as follows:

1) Make measurements $R(r_0)$ on the boundary of the body.

2) Find $\sigma$ on the boundary at $r_0$. For this we use the formula $$\sigma(\Theta) = \frac{\text{voltage at } \Theta \text{ for homogeneous case}}{\text{voltage at } \Theta \text{ computed from } R} \quad (2.1)$$

The voltages used here are the ones corresponding to the highest available spatial frequency, because they are the ones most sensitive to conductivity variations near the surface.

3) We propagate R into the interior by means of the formula $$R(r_0 - \Delta) = R(r_0) - \Delta \frac{\partial R}{\partial r}, \quad (2.2)$$

where $$\frac{\partial R}{\partial r} = \frac{1}{\sigma} + \frac{R}{r} + \frac{R}{r^2} \frac{\partial}{\partial \Theta}\left(\sigma \frac{\partial R}{\partial \Theta}\right). \quad (2.3)$$

4) Replace $r_0 - \Delta$ and repeat, starting with step 2.

Figure 1:
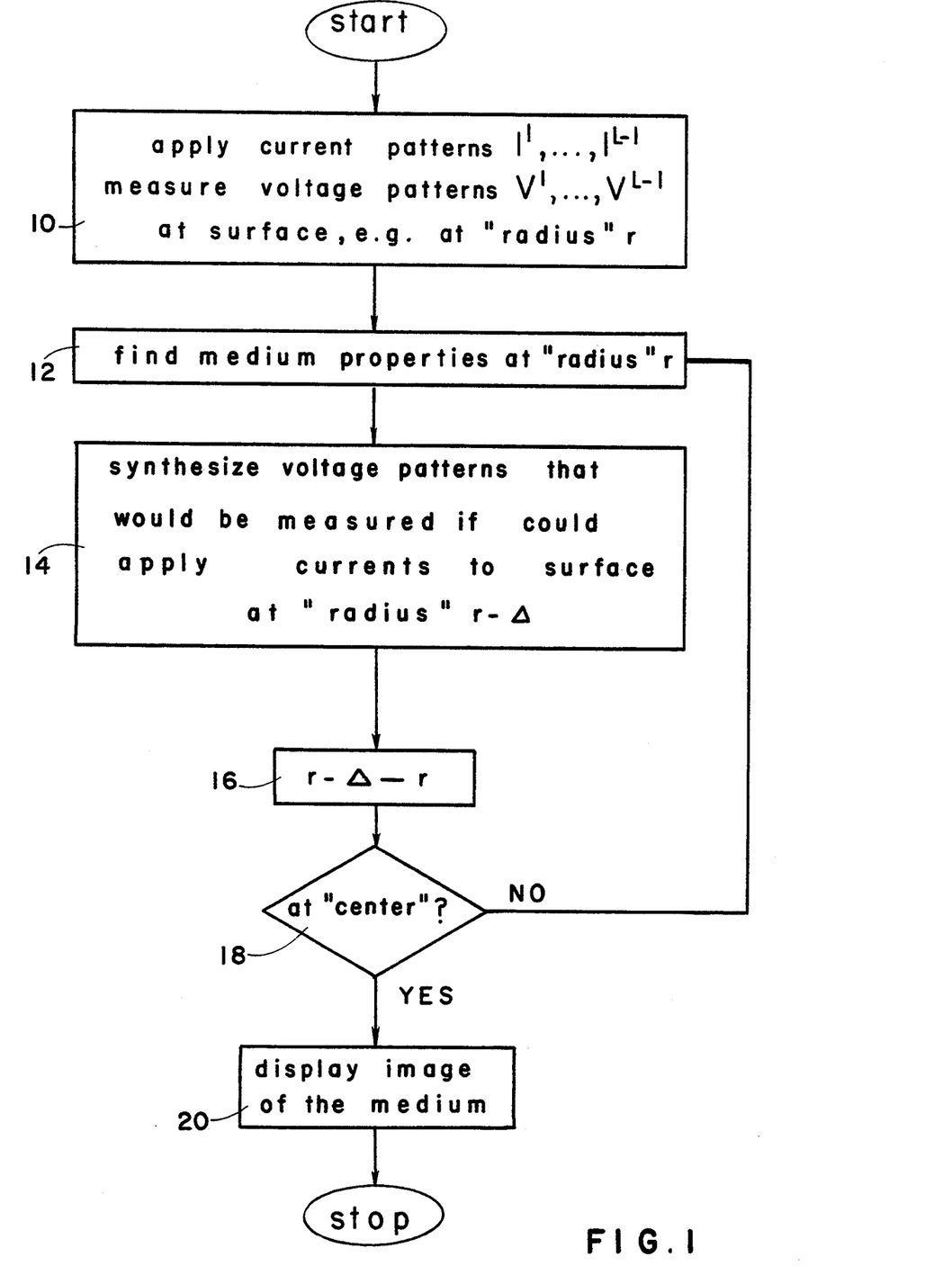
FIG. 1 is a flow chart illustrating the method of the invention.

FIG. 1 is a flow chart illustrating this layer stripping process.

The process starts at step 10 where a selected current pattern is applied to the outer boundary or surface of a body to be impinged and the resulting voltage pattern is measured. This can be done with the apparatus described in U.S. Pat. No. 4,920,490 or the apparatus disclosed in a U.S. patent application Ser. No. 07/591,615 filed Oct. 2, 1990, now U.S. Pat. No. 5,272,624, entitled CURRENT PATTERNS FOR IMPEDANCE TOMOGRAPHY, and owned by the assignee of the present application.

Although currents are applied and voltages measured, the invention operates equally well if voltages are applied and currents are measured.

The next step (12) finds the medium properties (such as conductivity characteristics) at the radius r from the data. This can be done in many ways. One way is to use formula (2.1) above. Another is to use formulas in a non-prior art article by the co-inventors entitled "A layer-stripping approach to impedance imaging", *Soc. for Computational Electromagnetic*, March 1991.

The next step (14) is to synthesize the voltages we would have measured if we could have applied currents to a surface with small radius $r - \Delta$. This can be done, for example: by formulas (2.2) and (2.3). Synthesizing the data at this inner surface could also be done by means of finite difference approximations to the interior fields.

We next set the radius to its new smaller value at 16, in preparation for repeating steps 12, 14 and 16 again. Before repeating steps 12, 14 and 16, however, we check to see if we have gone through the entire medium of body and reached its "center" at 18, or at least reached a desired depth in the body. If we have, the reconstruction is complete so the image can be displayed at 20 and the process stopped.

One of the advantages of the layer-stripping process of the invention is that it works in any geometry and in either two or three dimensions (or more, if more are ever needed). The above explanation merely illustrates the process in the simplest case of a two-dimensional disk. This is why the words "radius" and "center" appear in quotes in the flow chart. In other geometries, the radius and center might not be appropriate quantities. In more general terms, the object is to move by a selected incremental distance inwardly of each previous layer until the entire body (or a desired part thereof) is analyzed.

Figure 4:
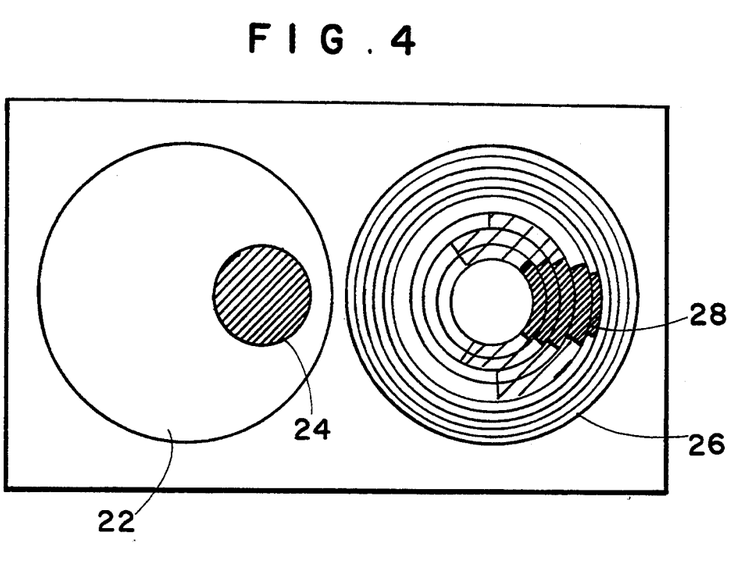
FIG. 4 is a representation of a side-by-side comparison between the actual body and an impedance image constructed for the body using the present invention.

FIG. 4 illustrates an actual disk-shaped body 22 containing water and a target 24 of different conductivity which was used to test the invention. The resulting image is shown at 26 which includes a target image 28.

The flow chart in FIG. 1 explains the main step in the process. However, when implemented in this simple way, the process tends to produce wild oscillations, and some way of stabilizing the oscillations is needed. Such a stabilizing method is called regularization. One possible regularization method is explained in the flow chart of FIG. 2.

Figure 2:
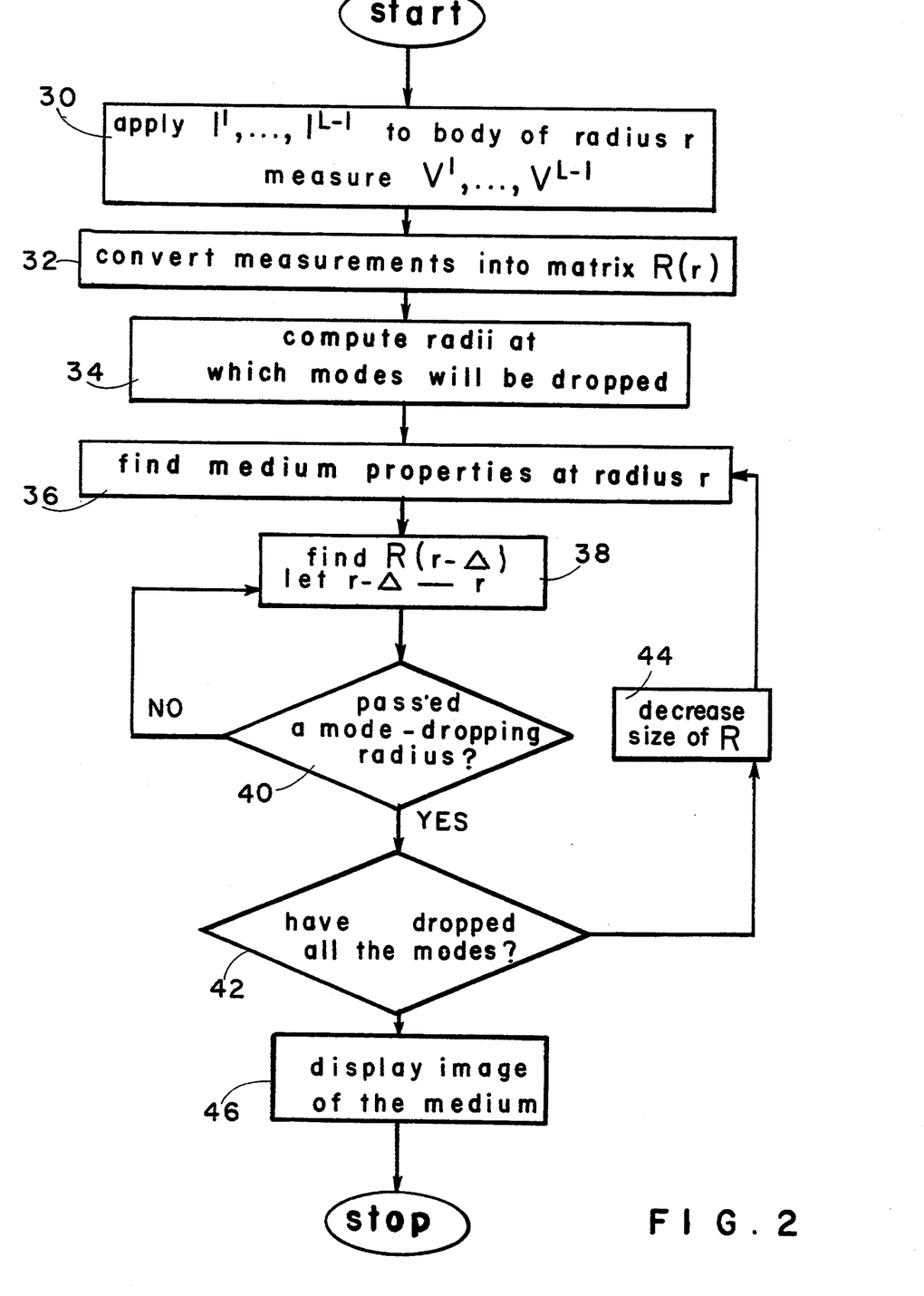
FIG. 2 is a flow chart similar to FIG. 1 illustrating a particular embodiment of the method which includes a regularization technique for the calculated data.

The first step 30 is to apply patterns of current to the body and measure the corresponding voltage patterns as with step 10 in FIG. 1.

The second step 32 is to assemble these measurements into a matrix R. One way to do this is to consider R as the matrix of the linear transformation that takes current patterns (each current pattern being a vector of numbers, each number representing a current) to voltage patterns (also a vector). This can be done by applying to the body a basis of current patterns, and then expressing the resulting voltage patterns in the same basis. Many different bases could be used here. In tests of the invention, we have used the basis of discrete trigonometric functions. Thus we apply trigonometric current patterns, and decompose the resulting voltage patterns into their discrete Fourier series. These Fourier coefficients form the matrix R. The index of the highest Fourier modes used will be referred to as the number of modes. If bases other than the discrete trigonometric ones are used, then the number of modes is related to the number of basis vectors used.

The matrix R can also be obtained by other means, using mathematical models to account for the presence of the electrodes.

The next step 34 is part of the regularization, which in this embodiment, is done by dropping Fourier modes at appropriate places. In step 34 we compute the radii at which we will drop Fourier modes. The concept here is that the current patterns which oscillate most rapidly in space, which are the patterns with higher Fourier modes, contain little information about the center of the body. As noted above roughly the nth Fourier mode contains almost no information about the region of the body inside the radius $$r_n = r_B n^{\frac{1}{2}n}(r_a/r_B)^{1/n} \quad (3)$$

where $r_B$ denotes the radius of the body $r_a$ denotes the radius of the smallest detectable object, whose size depends on the measurement precision. Thus the nth mode should be dropped at radius $r_n$. Other formulas can be used for $r_n$, but the basic concept is that a mode should be used only so long (i.e., as far into the body) as it contains information about that region of the body.

The next step 36 is to find the medium properties at the radius r from the matrix R(r). This can be done in the same way as step 12 in FIG. 1.

The next step 38 is to synthesize the data we would have measured if we could have applied currents to a surface with smaller radius $r-\Delta$. This can be done like steps 14 and 16 in FIG. 1.

Next, step 40 checks to see whether we have passed a mode-dropping radius. If not, we can either continue by synthesizing the data at a new surface at step 38, or by finding the medium parameters at 36 and then synthesizing at a new surface at 38. If it is time to drop another mode (42), we drop one at 44, find the medium parameters (36) and continue unless we have already dropped all the modes. If we have dropped them all, we can go no further, so we display the image at 46, which in our tests, has been done by a separate program together with the graphics package "Imagetool".

Figure 5:
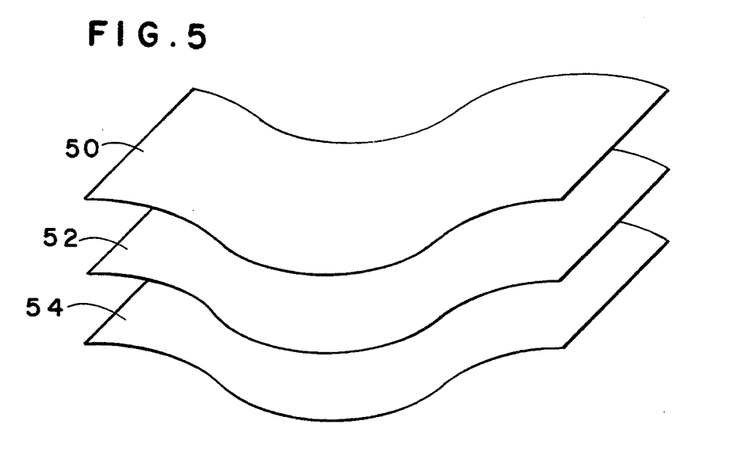
FIG. 5 is a schematic representation of a different layer pattern which can be utilized to image a differently configured body.
Figure 6:
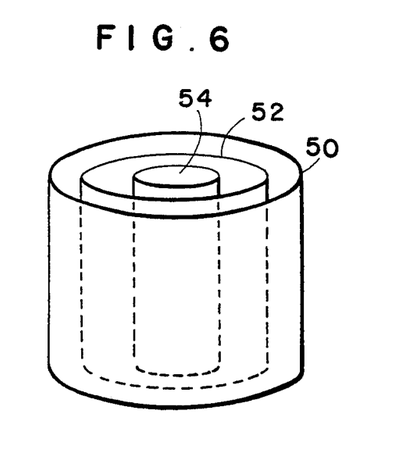
FIG. 6 is a view similar to FIG. 5 showing a further layer and body configuration which can be analyzed using the present invention.
Figure 7:
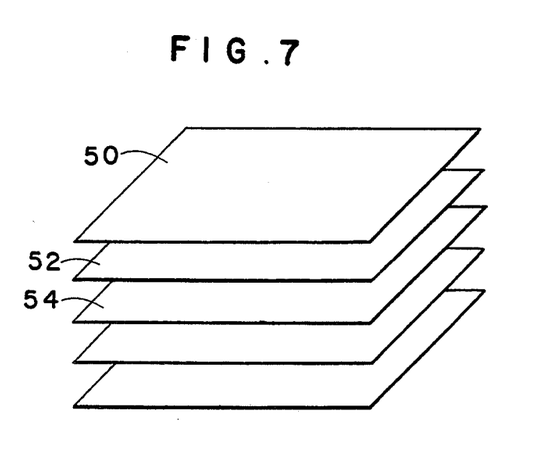
FIG. 7 is a view similar to FIG. 6 of a still further layer and body configuration which can be analyzed and imaged using the present invention.

FIGS. 5, 6 and 7 illustrate three additional configurations, other than a disk, which can be imaged using the present invention by simply changing trigonometric requirements from a radius and incremental change in radius, to the appropriate geometry for the outer boundary surface and condition, which is followed by successive inner boundaries at selected incremental distances inwardly from the outer boundary. In FIGS. 6 and 7 the outer boundary is at 50, the first inner boundary is at 52 and the second inner boundary is at 54.

Figure 3:
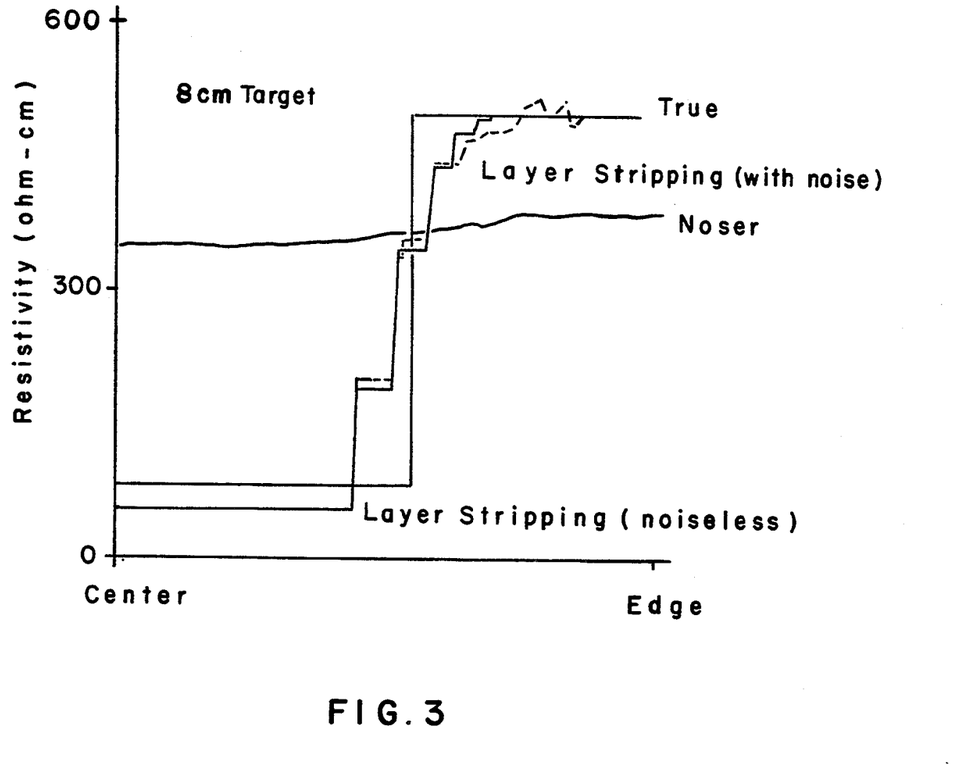
FIG. 3 is a graph plotting resistivity against layer position for a disk shaped body which was imaged using the present invention.

The results of reconstruction achieved with the present invention using simulated data are illustrated in connection with FIG. 3. FIG. 3 compares various reconstructions for a rotationally invariant distribution.

The curves shown are resistivity ($=1/\sigma$) versus radius for the true distribution, for a linearized reconstruction (NOSER: see M. Cheney, D. Isaacson, J. Newell, J. Goble, and S. Simske, "NOSER: An algorithm for solving the inverse conductivity problem": *Internat. J. Imaging Systems and Technology* 2 (1990) 66–75), for the layer-stripping method applied to data with 0.001% added noise.

Many variations of the layer-stripping process are possible. For example, it is not necessary to use the operator R; instead the operator R divided by the radius can be used. Alternatively, the inverse of the operator R can be used. (This corresponds to applying voltages and measuring either currents or charge.) All that is really needed is a set of current (or charge) patterns and their corresponding resulting voltage patterns (or vice versa). Use of the operator R merely provides a convenient way to organize this information.

Moreover, there are many ways to synthesize the subsurface measurements. In making the images shown here, the inventors used a simple finite difference approximation ("Euler method") to obtain an approximate solution to a differential equation (which is a Riccati equation). Instead of solving this Riccati equation by the Euler method, a predictor-corrector or other higher order scheme could be used. Alternatively, the subsurface measurements can be synthesized via two steps: a) find the measurements on the outer surface that would have resulted if the medium in the layer had been replaced by one in which the conductivity were constant and the permittivity were zero; b) solve a boundary valve problem to synthesize the measurements on the inner surface. (See, M. Cheney and D. Isaacson, Invariant imbedding, layer-stripping, and impedance imaging", to appear in the proceedings of a special session of the meeting of the American Mathematical Society, held in April 1990). Finally, the subsurface measurements could be synthesized by making finite difference approximations to the fields themselves.

There are also many ways to obtain the medium parameters at a layer from the actual or synthesized measurements at that layer. In making the images shown here, the inventors have used the ratio of actual or synthesized voltages to the corresponding voltages for a homogeneous body (See, M. Cheney, D. Isaacson, E. J. Somersalo, E. L. Isaacson, and E. J. Coffey, "A layer-stripping reconstruction algorithm for impedance imaging", submitted to 13th Annual Conference of IEEE Engineering in Medicine and Biology Society, for publication November 1991). However, a ratio of Green's functions could also be used (see M. Cheney, D. Isaacson, E. Somersalo and E. L. Isaacson, "A layer-stripping approach to impedance imaging", in the 7th Annual Review of Progress in Applied Computational Electromagnetics, March 1991). The measured or synthesized measurements at a layer can also be combined in many other ways to obtain an approximation to the medium parameters.

The layer-stripping method of the invention is a noniterative method for getting an approximate solution to the full nonlinear inverse problem. In some examples, it outperforms linearizod algorithms. Moreover, it has the following possible advantages. First, is has no difficulty with extraneous local minima as do optimization-type methods. Second, in principle at least, it solves the full nonlinear problem. Third, it requires fewer computations and less storage than optimization-type methods. Fourth, with only minor modification of the process shown here, it can be used for different geometries and for three-dimensional problems.

The chief difficulty, of course, stems for the fact that the inverse problem is ill-posed: large changes in the conductivity can correspond to very small changes in the boundary measurements. This ill-posedness appears in the above algorithm as instability: the reconstructed conductivity tends to oscillate wildly as noted above. In order to make the images shown here, we used carefully chosen regularization, explained above.

A more comprehensive mathematical explanation of the principles of the invention is contained in an article entitled "Layer Stripping: A Direct Numerical Method For Impedance Imaging", by E. Somersalo, M. Cheney, D. Isaacson and E. Isaacson, *Inverse Problems* 7, pp. 900–903, 905–907, 911–912, 914, 922 and 923, December 1991.

While specific embodiments of the invention have been shown and described in detail to illustrate the application of the principles of the invention, it will be understood that the invention may be embodied otherwise without departing from such principles.

THEORETICAL DISCUSSION

In Part 1, we discuss the theoretical background necessary to understand the algorithm. Part 2 describes the algorithm itself in a simple geometry, and contains a discussion of the numerical tests that we have run.

PART 1

The inversion method is based on two separate steps, namely 1) the reconstruction of the conductivity at the boundary and 2) the propagation of the measurement through the medium. We dedicate one section to each one of these steps.

1.1 Reconstruction at the Boundary

We start this section by stating the inverse problem under consideration.

We denote the body by $\Omega$ for $\subset R^n$, $n=2$ or $3$, and the conductivity by $\sigma$. The electric potential $u$ satisfies $$\begin{cases} \nabla \cdot \sigma \nabla u = 0 & \text{in } \Omega, \\ \sigma \frac{\partial u}{\partial \nu} = j & \text{on } \partial \Omega, \end{cases} \quad (1.1.1)$$

where $j$ denotes the current density applied to the boundary $\partial \Omega$. In order for a solution of (1.1.1) to exist, $j$ must satisfy the conservation of charge condition $$\int_{\partial \Omega} j \, dS = 0. \quad (1.1.2)$$

Solutions of (1.1.1) are determined only up to an additive constant; choosing this constant corresponds to specifying the ground or reference potential. We do this by means of the condition $$\int_{\partial \Omega} u|_{\partial \Omega} \, dS = 0. \quad (1.1.3)$$

We make the following assumptions. 1) The body $\Omega$ consists of an open, connected, simply connected, bounded set whose boundary $\partial \Omega$ consists of a single smooth curve. 2) The conductivity $\sigma$ is a real valued strictly positive function in $\overline{\Omega}$. To avoid extra complications, we assume that $\sigma$ is smooth. This assumption can be relaxed; e.g. $\sigma \in C^3(\overline{\Omega})$ would be enough, and most of the results apply even for less smooth functions. 3) The current density $j$ is a function in $H^s(\partial \Omega)$ for $s \geq \frac{1}{2}$, i.e., $j$ is in the $L^2$-based Sobolev space with smoothness index $s$. It follows that the electric potential $u$ is $H^{s+3/2}(\Omega)$.

We assume that we can make any measurements we like. Thus, for any current density $j$, we assume that we can measure the corresponding voltage $u|_{\partial \Omega}$. In other words, we know the map $$R: j \rightarrow u|_{\partial \Omega},$$

which we call the resistive map. Thus $R$ is a map between the following spaces:

$$R: H^s(\partial \Omega) \rightarrow H^{s+1}(\partial \Omega).$$

(In fact both the domain of $R$ and its range are the closed subspaces of the Sobolev spaces where the integral constraints (1.1.2)–(1.1.3) are valid.) We denote by $R_o$ the resistive map in the case when $\sigma$ is identically one.

The inverse boundary value problem that we seek to solve numerically is to reconstruct $\sigma$ from the partial knowledge of the operator $R$ on $\partial \Omega$.

The reason we work with the mapping $R$ instead of its inverse, the Dirichlet-to-Neumann mapping, is that measuring the voltages corresponding to known current densities is in practice a more stable procedure than the reverse.

We next establish a formula for reconstructing $\sigma$ on the boundary $\partial \Omega$ from the resistive map. It is known that this reconstruction problem is uniquely solvable in a constructive manner. We present here a simple calculation that gives an formula for this.

We consider the Neumann problem $$\begin{cases} \nabla \cdot \sigma \nabla u = f & \text{in } \Omega \\ \sigma \frac{\partial u}{\partial \nu} = j & \text{on } \partial \Omega, \end{cases} \quad (1.1.4)$$

where $f$ and $j$ are subject to the integral constraint $$\int_\Omega f \, dx = \int_{\partial \Omega} j \, dS.$$

This condition is required to guarantee the existence of the solution. We denote by $T\sigma$ the map $$T\sigma(f, j) = u.$$

For $s \geq 0$, we have $$T\sigma: H^s(\Omega) \times H^{s+\frac{1}{2}}(\partial \Omega) \rightarrow H^{s+2}(\Omega) \quad (1.1.5)$$

We note that $T\sigma$ is related to the resistive map $R$ by taking $f=0$ and restricting $u$ to the boundary. Thus $$R = \gamma T\sigma |\{o\} \times H^{s+\frac{1}{2}}(\partial \Omega),$$

where $\gamma$ is the trace mapping $$\gamma: u \rightarrow u|_{\partial \Omega},$$

which maps $$\gamma: H^s(\Omega) \rightarrow H^{s-\frac{1}{2}}(\partial \Omega),$$

where $s > \frac{1}{2}$. In the following, let $s \geq 0$ and $T\sigma$ be the mapping $$T\sigma: H^s(\Omega) \times H^{s+\frac{1}{2}}(\partial \Omega) \rightarrow H^{s+2}(\Omega), \quad T\sigma(f,j)=u,$$

that assigns to the pair $(f,j)$ the solution of the Neumann problem (1.1.4). We write $T$ for $T\sigma$ when $\sigma=1$ identically.

1.1.1 Proposition

The operator $T\sigma$ admits a decomposition $$T\sigma = \frac{1}{\sigma} T + T_R, \quad (1.1.6)$$

where $T_R$ is a mapping $H^s(\Omega) \times H^{s+\frac{1}{2}}(\partial \Omega) \rightarrow H^{s+3}(\Omega)$, $s \geq 0$.

Proof: Let $u = T\sigma(f,j)$ and $u_o = T(f,j)$. We want to show that the difference $$u_R = u - \frac{1}{\sigma} u_0$$

is smoother than $u$, which is itself in $H^{s+2}$. To do this, we note that $u_R$ satisfies $$\begin{cases} \nabla \cdot \sigma \nabla u_R = \nabla \cdot (u_0 \nabla a) & \text{in } \Omega, \\ \sigma \frac{\partial u_R}{\partial \nu} = u_0 \frac{\partial a}{\partial \nu} & \text{on } \partial \Omega, \end{cases}$$

where $a = \log \sigma$. We can therefore write $u_R$ in terms of the composition of maps $$u_R = T\sigma B u_0 = T\sigma B T(f,j), \quad (1.1.7)$$

where $B$ denotes the mapping $$B\phi = \left(\nabla \cdot (\phi \nabla a), \phi|_{\partial\Omega} \frac{\partial a}{\partial \nu}\right).$$

The map B maps between the spaces $$B: H^{s+2}(\Omega) \to H^{s+1}(\Omega) \times H^{s+3/2}(\partial\Omega) \tag{1.1.8}$$

This mapping property together with (1.1.5) shows that $u_R$ is in $H^{s+3}$. In terms of the T operators, we can write (1.1.7) as $$T\sigma = \frac{1}{\sigma} T + T\sigma BT = \frac{1}{\sigma} T + T_R.$$

We have shown that the operator $T_R$ has the claimed mapping properties.

We convert (1.1.6) into information about R by taking f=0 and restricting to the boundary. Thus we have $$R = \gamma T_s|_{\{0\} \times H^{s+\frac{1}{2}}(\partial\Omega)} = \tag{1.1.9}$$

$$\gamma \frac{1}{\sigma} T|_{\{0\} \times H^{s+\frac{1}{2}}(\partial\Omega)} + \gamma T_R|_{\{0\} \times H^{s+\frac{1}{2}}(\partial\Omega)} = \frac{1}{\sigma} \Big|_{\partial\Omega} R_o + R_R,$$

where $R_R$ is defined to be the last term in the first line of (1.1.9). Clearly, $R_R$ maps $H^{s+\frac{1}{2}}(\partial\Omega)$ to $H^{s+5/2}(\partial\Omega)$, so the principal part of the operator R is just $(1/\sigma)R_o$. In the following example, the explicit form of $R_o$ is given in a simple geometry.

1.1.2 Example.

Let $\Omega$ be a unit disc in $R^2$. In this case, $u_o$ satisfying $$\begin{cases} \Delta u_o = 0 & \text{in } \Omega, \\ \frac{\partial u_o}{\partial r} = j & \text{on } \partial\Omega \end{cases} \tag{1.1.10}$$

is explicitly solvable. This problem is separable in the polar coordinates $(r,\theta)$, so we can write the solution as $$u_o(r,\theta) = \sum_{m=-\infty}^{\infty}{}' \alpha_m r^{|m|} e^{im\theta},$$

where the prime on the sum indicates that the m=0 term is omitted. The boundary condition of (1.1.10) implies $$\sum{}' |m| \alpha_m e^{im\theta} = j(\theta).$$

If we expand j in its Fourier series, with $j_m$ being the mth Fourier coefficient of j, then we have $$\alpha_m = \frac{1}{|m|} j_m.$$

Hence, the principal symbol of the operator $R_o$, denoted as $\sigma_1(R_o)$, is $$\sigma_1(R_o)(\theta,n) = \frac{1}{|n|}.$$

(1.1.9) we then obtain for the principal symbol of R:

$$\sigma_1(R)(\theta,n) = \frac{1}{|n|\sigma(1,\theta)}. \tag{1.1.11}$$

If we denote by $R_{m,n}$ the matrix element of R in the Fourier basis, we have $$R_{m,n} = (e^{im\theta}, Re^{in\theta}) = \frac{1}{|n|} \rho_{m-n} + O\left(\frac{1}{|n|^2}\right),$$

where $$\rho_n = \frac{1}{2\pi} \int_U^{2\pi} e^{-in\theta} \frac{1}{\sigma(1,\theta)} d\theta.$$

Hence, the high frequency limit of R gives the function $1/\sigma$ at the boundary.

1.1.3 Remark

In a more complex geometry than that of the previous example, the principal part of R must be calculated in local coordinates. If $p_o$ is a point on $\partial\Omega$ and U is a coordinate neighborhood of $p_o$ such that in the local coordinates $(x^1, x^2, \ldots, x^n) = (x'; x^n)$, the boundary is given by $\partial\Omega \cap U = \{(x'; x^n) | x^n = 0\}$, then the principal symbol of R is $$\sigma_1(R)(x',\xi') = \frac{1}{|\xi'|} \frac{1}{\sigma(x';0)},$$

where $\epsilon'$ is the dual coordinate of $x'$. For a related calculation, 1.2 Propagation through the Body Once the conductivity is determined at the boundary from the high frequency behaviour of the mapping R, the next step is to propagate R through the reconstructed boundary layer, We do this by means of a differential equation that R satisfies. This differential equation, which is of the Riccati type, is discussed below. Similar Riccati equations have been obtained for scattering data of hyperbolic inverse boundary value problems in one space dimension, A closely related Riccati-type formula was previously found for the Schrödinger operator.

For the sake of clarity, we drive the Riccati equation for R only in a spherical domain, this avoiding the use of local coordinate systems. Therefore, let $\Omega$ be either a unit ball in $R^3$ or a unit disc in $R^2$. If r is the radial coordinate in $\Omega$, we denote by $\Omega_r$ the domain $\{x: |x| < r\}$, $0 < r \leq 1$, and $\Omega_1 = \Omega$. For each r, we can now solve the boundary value problem $$\begin{cases} \nabla \cdot \sigma \nabla u = 0 & \text{for } |x| < r, \\ \sigma \frac{\partial u}{\partial r} = j & \text{for } |x| = r, \end{cases} \tag{1.2.1}$$

where j satisfies the conservation of charge constraint (1.1.2). As before, the solution u is unique if we impose the condition (1.1.3) to specify a choice of ground potential. This again enables us to define the family of operators, $R_r j \to u | \partial \Omega_r,$ (1.2.2)

which have the mapping properties
$R_r: H^s(S^{n-1}) \to H^{s+1}(S^{n-1}),$ $s \geq \frac{1}{2}$. Note that we have identified the boundary of $\Omega_r$ with the unit circle $S^1$ if $n=2$ and with the unit spheres $S^2$ if $n=3$. The original R is now denoted by $R_1$.

To understand how $R_r$ changes with r, we simply differentiate (1.2.2) with respect to r. This gives us $$\partial_r u = (\partial_r R) j + R(\partial_r j). \quad (1.2.3)$$

The last term of (1.2.3) contains the expression $$\partial_r j = \partial_r \sigma \partial_r u,$$

which arises in the polar form of the differential equation (1.2.1). In the two-dimensional case this polar form is $$\partial_r \sigma \partial_r u + \frac{\sigma}{r} \partial_r u + \frac{1}{r^2} \partial_\theta \sigma \partial_\theta u. \quad (1.2.4)$$

We therefore use (1.2.4) in (1.2.3), obtaining $$\partial_r u = (\partial_r R) j - R\left(\frac{\sigma}{r} \partial_r u\right) - R\left(\frac{1}{r^2} \partial_\theta \sigma \partial_\theta u\right). \quad (1.2.5)$$

Finally, we use the boundary condition of (1.2.1) in (1.2.5), which gives $$(\partial_r R) j = \frac{j}{\sigma} + \frac{1}{r} R j + \frac{1}{r^2} R(\partial_\theta \sigma \partial_\theta R j). \quad (1.2.6)$$

In the above calculation, we have assumed that $R_r$ is differentiable. The following theorem makes precise the sense in which this derivative exists, and gives the form of the Riccati equation in higher dimensions.

1.2.1 Theorem.

The operators $R_r$, $0 < r \leq 1$, form a left continuous family with respect to r in the strong operator topology of $L(H^s(S^{n-1}), H^{s+1}(S^{n-1}))$, $s \geq 3/2$. Moreover, the strong limit $$\lim_{\sigma \to 0+} \frac{1}{\delta}(R_r - R_{r-\delta}) = D_r R_r$$

exists in $L(H^s(S^{n-1}), H^s(S^{n-1}))$, and it satisfies $$D_r R_r = \frac{1}{\sigma} + \frac{n-1}{r} R_r + R_r \nabla_T \cdot \sigma \nabla_T R_r, \quad (1.2.6)$$

where $\nabla_T \cdot \sigma \nabla_T$ is the tangential part the operator $\nabla \cdot \sigma \nabla$ along the surface $|x| = r$.

Proof: First we prove the continuity claim. Let u be a solution of (1.2.1). We write $(R_r - R_{r-\delta}) j = (R_r j - u||x|=r-\delta) + (u||x|=r-\delta - R_{r-\delta} j) =$
$(u||x|=r - u||x|=r-\delta) + R_{r-\delta}(\sigma \partial_r u||x|=r-\delta - \sigma \partial_r u||x|=r).$ But a slight modification shows that $\| u||x|=r - u||x|=r-\delta \|_{H^{s+1}(S^{n-1})} \to 0,$ $\| \sigma \partial_r u||x|=r-\delta - \sigma \partial_r u||x|=r \|_{H^s(S^{n-1})} \to 0,$ as $\delta$ tends to zero. Since the family $\{R_{r-\delta}\}$ is bounded for $\delta$ small, the continuity claim follows.

To show the differentiability, we have to show that $$\frac{1}{\delta}(u||x|=r - u||x|=r-\delta) \to \partial_r u||x|=r \text{ in } H^s(S^{n-1}),$$

and similarly, $$\frac{1}{\delta}(\sigma \partial_r u||x|=r - \sigma \partial_r u||x|=r-\delta) \to \partial_r \sigma \partial_r u||x|=r \text{ in } H^{s-1}(S^{n-1}),$$

These limits follow again by the continuity of the trace operator with respect to r. Indeed, if we consider the case $r=1$, we have $\| \frac{1}{\delta}(u||x|=1 - u||x|=1-\delta) - \partial_r u||x|=1 \|_{H^s(S^{n-1})} =$ $\| \frac{1}{\delta} \int_{1-\delta}^{1} \partial_r u||x|=r dr - \partial_r u||x|=1 \|_{H^s(S^n)} \leq$ $\frac{1}{\delta} \int_{1-\delta}^{1} \| \partial_r u||x|=r - \partial_r u||x|=1 \|_{H^s(S^{n-1})} dr \to 0.$ The second limit follows in the same way, by replacing u with $\sigma \partial_r u$ in the above argument.

Finally, to get the differential equation for $R_r$, we note that $$D_r R_r j = \partial_r u||x|=r - R_r(\partial_r \sigma \partial_r u)||x|=r = \quad (1.2.7)$$

$$\frac{1}{\sigma} j - R_r(\partial_r \sigma \partial_r u)||x|=r$$

by the above proof. On the other hand, $\Delta u \in H^{s+\frac{1}{2}}(\{|x|<1\})$, so the trace to $|x|=r$ exists in $H^s(S^{n-1})$, and $$\nabla \cdot \nabla u||x|=r = \left(\partial_r \sigma \partial_r u + \frac{n-1}{r} \sigma \partial_r u + \nabla_T \cdot \sigma \nabla_T u\right)||x|=r$$

$$= \left(\frac{\partial}{\partial r} \sigma \frac{\partial u}{\partial r}\right)||x|=r +$$

$$\frac{n-1}{r} j + \nabla_T \cdot \sigma \nabla_T R_r j = 0,$$

so solving for the second order radial derivative and substitute into equation (1.2.7) gives the claim.

Remark.

It is not hard to see how this result above could be generalized to an arbitrary geometry. Let $p_0 \in \partial \Omega$ and assume that U is a neighborhood of $p_0$ having local coordinates $x^1, \ldots, x^n$. We may assume that $\partial \Omega \cap U = \{(x'; x^n) | x^n = 0\}$, where $x' = (x^1, \ldots x^{n-1})$. Assume further that we have a one parameter family of surfaces $\Gamma_t$, $0 \leq t \leq 1$, that foliates U and is such that $\Gamma_0 = \partial \Omega \cap U$. Furthermore, we assume that the trajectory $t \to p(x'; t) \in U$ of each boundary point $(x'; 0) \in \partial \Omega \cap U$ intersects the surfaces $\Gamma_t$ perpendicularly, then $(x^1, \ldots, x^{n-1}, t)$ forms a new coordinate system in $U_{0 \leq t \leq 1} \Gamma_t$, with $g_{i,n} = \delta_{i,n} g_{n,n}$. Here, $g_{i,j}$ is the metric tensor, i.e., $ds^2 = g_{i,j} dx^i dx^j$ (FIG. 1). If we define $R_t$ as the Neumann-to-Dirichlet mapping on the boundary $\partial \Omega_t$ obtained by replacing $\Gamma_0$ by $\Gamma_t$, a straightforward modification of the proof of the previous theorem shows that $R_t$ satisfies $$D_t R_t = \frac{1}{\sigma} + (g^{n,n})^{1/2} R_t \sum_{i=1}^{n} \Gamma_{n,i}^i + (g^{n,n})^{1/2} R_t g_{n,n}^{1/2} \nabla_T \cdot \sigma \nabla_T R_t,$$

where $\Gamma_{n,i}^i$ is the Riemannian connection in the local coordinate system (x';t). We skip the details here.

The above remark together with Remark 1.1.3 gives the generalization of the layer-stripping algorithm to arbitrary geometry.

From now on, we confine ourselves to the case of a two-dimensional disc, $\Omega = \{x \in R^2 | |x| < 1\}$. To get an explicit matrix formulation of the Riccati equation (1.2.2), we write the equation in the Fourier basis. Therefore, consider two-dimensional version of the equation.

$$D_r R_r = \frac{1}{\partial} + \frac{1}{r} R_r + \frac{1}{r^2} R_r \partial_\theta \sigma \partial_\theta R_r.$$

If we define the operator $W_r = (1/r) R_r$, we find that $W_r$ satisfies the equation $$r D_r W_r = \frac{1}{\sigma} + W_r \partial_\theta \sigma \partial_\theta W_r.$$

Let $(w_{m,n}(r))$ be the Fourier representation of the operator $W_r$, i.e.

$$\omega_{m,n}(r) = \frac{1}{2\pi} \int_{-\pi}^{\pi} e^{-im\theta} W_r(e^{in\cdot})(\theta) d\theta.$$

Denoting by $\rho_n(r)$ and $\sigma_n(r)$ the Fourier coefficients of $1/\sigma(r,\theta)$ and $\sigma(r,\theta)$, we find that the matrix elements $w_{m,n}$ satisfy the equations $$r \frac{d\omega_{m,n}}{dr} = \rho_{m-n}(r) - \sum_{k,l=-\infty}^{\infty} \omega_{m,k} k \sigma_{k-l}(r) l \omega_{l,n}, \quad (1.2.8)$$

$$-\infty < n,m < \infty$$

This formula is the one that will be employed in the actual implementation of the algorithm later in Part 2 of this work.

1.2.2. Example

Before going to the actual implementation of the invention method, we consider briefly a special case: If the conductivity distribution $\sigma$ is rotationally invariant, i.e., $\sigma = \sigma(r)$, equation (1.2.8) takes an especially simple form. In this case, the exponentials $e^{in\theta}$ are the eigenfunctions of the operator $W_r$, so $$w_{m,n} = \delta_{m,n} w_n.$$

Equation (1.2.8) for the diagonal elements becomes then $$r \frac{d\omega_n}{dr} = \frac{1}{\sigma} - n^2 \sigma \omega_n^2. \quad (1.2.9)$$

Furthermore, if we make the rescaling of the variable r as $p = r^n$, and define $$y_n(p) = n w_n(p^{1/n}) = n w_n(r),$$

$$\sigma_n(p) = \sigma(p^{1/n}) = \sigma(r),$$

we get simply $$p \frac{dy_n}{dp} = \frac{1}{\sigma_n} - \sigma_n y_n^2. \quad (1.2.10)$$

To get an idea of the instability of the solutions $y_n$, consider the simple case where $\sigma_n$ remains constant in an interval $[p_0, p_1]$. In this case, equation (1.2.10) admits an explicit solution. We have $$\int_{y_n(p_0)}^{y_n(p_1)} \frac{dy_n}{1 - (\sigma_n y_n)^2} = \frac{1}{\sigma_n} \int_{p_0}^{p_1} \frac{dp}{p},$$

from which we find $$\log \frac{p_1}{p_0} = \frac{1}{2} \log \left| \frac{1 - \sigma_n y_n(p_0)}{1 + \sigma_n y_n(p_0)} \cdot \frac{1 + \sigma_n y_n(p_1)}{1 - \sigma_n y_n(p_1)} \right|.$$

Denoting by M the rational function $M(t) = (1-t)/(1+t)$, and using the fact that $M^{-1} = M$, we finally find that $$y_n(p_0) = \frac{1}{\sigma_n} M\left( \left( \frac{p_1}{p_0} \right)^2 M(\sigma_n y_n(p_1)) \right), \quad (1.2.11)$$

or, conversely $$y_n(p_1) = \frac{1}{\sigma_n} M\left( \left( \frac{p_0}{p_1} \right)^2 M(\sigma_n y_n(p_0)) \right). \quad (1.2.12)$$

In particular, assume that $\sigma$ and hence $\sigma_n$ is constant over the whole interval [0, 1]. Then the solution of the equation (1.2.10) that corresponds to the physical nth eigenvalue of the operator W is found to be $$y_n = \frac{1}{\sigma}.$$

Assume, however, that we seek to solve $y_n$ numerically starting with a boundary value $y_n(1)$ that contains measurement errors. We may write $$y_n(1) = (1 + \epsilon) \frac{1}{\sigma}.$$

Assuming that we keep the value of $\sigma$ fixed in the equation (1.2.9), the solution $y_n$, as the step size of the numerical scheme decreases, converges to $$y_n(r) = \frac{1}{\sigma} M\left( \frac{1}{r^{2n}} M(1 + \epsilon) \right).$$

It is easy to see that r reaches a critical value $r^*_n$, where $y_n(r)$ either becomes negative or infinite, depending on the sign of $\epsilon$, at $$r_n^* = \left( \frac{|\epsilon|}{2 + \epsilon} \right)^{1/2n}. \quad (1.2.13)$$

From this simple example we see that in general, the numerical determination of the higher modes becomes less and less stable as the number of the mode increases. This principle can be used as a guideline in designing the numerical algorithm.

PART 1

In this part, we explain the numerical algorithm to solve the impedance imaging problem. Section 1 describes the algorithm and in Section 2, we discuss the choice of various parameters, the convergence and the performance of it in the light of the numerical tests that we have run.

Throughout this part, $\Omega$ is the unit disc.

2.1 Description of the Algorithm

We start with the numerical data consisting of the matrix elements of the operator $W_r$ at the boundary in the Fourier basis (see formula (1.2.3)). If N is the number of the highest Fourier mode available, the initial data set is $$D(1,N) = \{w_{n,m}(1) \mid -n \leq n, m \leq N\},$$

the numbers $w_{n,m}$ including possible numerical or measurement errors. In $D(1,N)$, the first variable 1 refers to the value of r.

The reconstruction of the conductivity proceeds through the following steps:

Step 1. Choose first a decreasing sequence of radii $\alpha_i$, $0 \leq i \leq N+1$, i.e., $$0 = \alpha_{N+1} < \alpha_N < \ldots < \alpha_0 = 1,$$

and divide the disc $\Omega$ into rings $\Omega_i$, $$\Omega_i = \{x \in R^2 \mid \alpha_i < |x| \leq \alpha_{i-1}\}, \ 1 \leq i \leq N.$$

Step 2. Estimate the resistivity $\rho = 1/\sigma$ at the outer boundary of $\Omega_1$ by using the reconstruction formula of Example 1.1.2. Since $$\omega_{m1 \pm N} = \frac{1}{N} \rho_{m \mp N} + O\left(\frac{1}{N^2}\right),$$

we obtain an approximation for $\rho(1,\theta)$ by writing $$\rho(1,\theta) \approx \sum_{k=-N}^{N} \rho_k e^{ik\theta}$$
$$= \frac{N}{2}(\omega_{-N,-N} + \omega_{N_1 N}) +$$
$$N \sum_{k=1}^{N} (\omega_{N-k_1 N} e^{-ik\theta} + \omega_{k-N_1-N} e^{ik\theta}).$$

Having this approximation for $\rho$, we write simply $$\sigma(1,\theta) = \frac{1}{\rho(1,\theta)},$$

and calculate the Fourier coefficients $\sigma_n$, $-N \leq n \leq N$, of $\sigma$ for later use. We retain the Fourier coefficients of $\rho$ and $\sigma$ and assume that $\rho_n = \sigma_n = 0$, if $|n| > N$.

Step 3. Assume that $\sigma(r,\theta) = \sigma(1,\theta)$ and $\rho(r,\theta) = \rho(1,\theta)$ in the whole ring $\Omega_1$, i.e., for $\alpha_1 < r < \alpha_0$. Choose a step size $\Delta < \alpha_o - \alpha_1$, and propagate the matrix elements $w_{m,n}$, $-N+1 \leq m,n \leq N-1$ through the ring $\Omega_1$ by applying e.g. the Euler method to the differential equation for $w_{m,n}$, i.e., $$\omega_{n,m}(1-\Delta) \approx \omega_{m,n}(1) - \Delta_1 \frac{d\omega_{m,n}}{dr} \quad (1)$$
$$= \omega_{m,n} -$$
$$\Delta \left( \rho_{m-n} - \sum_{k,l=-N+1}^{N-1} \omega_{m,k}(1) k \sigma_{k-1} l \omega_{l,n}(1) \right)$$

repeating the step until an approximation for $w_{m,n}(\alpha_1)$, $-N+1 \leq m,n \leq N-1$, is obtained. Thus we have a new data set $$D(N-1, \alpha_1) = \{w_{m,n}(\alpha_1) \mid -N+1 \leq m,n \leq N-1\}.$$

Now we go back to the beginning of Step 2, replacing N by N−1 and $\alpha_0$ by $\alpha_1$ everywhere, and repeating the procedure we find an approximation for $\sigma$ everywhere in $\alpha_N < r < 1$. Finally, in the set $\Omega_N$ we set $$\sigma = \frac{1}{2\pi \alpha_N} \int_{-\pi}^{\pi} \sigma(\alpha_N, \theta) d\theta.$$

2.2 Numerical Tests and Discussion

To test the algorithm, we start with the simplest case, where $\sigma$ is rotationally invariant, i.e.: $\sigma = \sigma(r)$. The number N of Fourier modes in the data set was chosen to be N=16. The reason for this choice is to get reference material for later tests with measurements done with the device described in the test phantom has a circular tank with 32 electrodes attached to its boundary.

In the rotationally invariant case, we have a diagonal data matrix $$w_{m,n}(1) = \delta_{m,n} w_n, \ -N \leq m,n \leq N,$$

as explained in Section 2.1. Furthermore, the steps 2 and 3 simplify considerably: we have $$\frac{1}{\sigma(1)} = \frac{N}{2}(\omega_{-N} + \omega_N),$$

and the differential equations are uncoupled.

Evidently, the first problem to solve is to decide how to choose the radii, $\alpha_i$, where the higher nodes are dropped. A natural, but naive, choice would be equally spaced points between the center and the edge. However, there is an argument that supports a different choice of the parameters $\alpha_1$. Consider a conductivity distribution of the form $$\sigma(r) = \begin{cases} \sigma_0, & \text{as } r \leq r_1, \\ \sigma_1, & \text{as } r_1 < r \leq 1. \end{cases}$$

If we apply the current density $j_n(\theta) = e^{in\theta}$ at the boundary $r=1$, the corresponding voltage at $r=1$ is $$u(1,\theta) = \frac{1}{|\eta|\sigma_o} \frac{1 - \mu r_1^{2|n|}}{1 + \mu r_1^{2|n|}} e^{in\theta},$$

where $$-1 < \mu = \frac{\sigma_0 - \sigma_1}{\sigma_0 + \sigma_1} < 1.$$

Let $u_0$ be the solution in the case of a homogeneous body, i.e., $\mu=0$. The difference of the voltage when $j_n$ is applied can be estimated as $$|u(1,\theta) - u_0(1,\theta)| = \frac{1}{|n|\sigma_0} \frac{|\mu|r_1^{2|n|}}{|1+\mu r_1^{2|n|}|} \leq$$

$$\frac{1}{|n|\sigma_2} \frac{r^{2|u|1}}{1-r_1^{2|n|}}.$$

Assume that the measurement precision at the frequency n is $\epsilon_n$. Clearly, then the critical size $r_n$ of an object at the center of the body that still contributes a measurable difference to the voltage at this frequency is obtained by solving the equation $$\frac{1}{|n|\sigma_0} \frac{r_n^{2|n|}}{1-r^{2|n|}{}_n} = \epsilon_n$$

for $r_n$, yielding $$r_n = \left(\frac{|n|\sigma_0\epsilon_n}{1+|n|\sigma_0\epsilon_n}\right)^{1/2|n|}. \qquad (2.2.1)$$

Objects smaller than this radius $r_n$ are beyond sight at this mode.

In particular, if we assume that $\epsilon=|n|\sigma_0\epsilon_n=$constant, we get $$r_n = \left(\frac{\epsilon}{1+\epsilon}\right)^{1/2|n|} = r_1^{1/n}. \qquad (2.2.2)$$

(Note the close relationship with the formula (1.2.7) of $r^*_n!$.)

Since the radii $a_i$ are used in the algorithm to determine where we discard the higher modes no longer useful for the reconstruction, the formulas (2.2.1) and (2.2.2) should be used as guidelines for this choice.

The following examples illustrate the performance of the method. We assumed that the body has a constant conductivity $\sigma=0.5$. The stepsize $\Delta_n$ appearing in the reconstruction step 3 is kept fixed, $\Delta_n=\Delta=0.01$.

For the first reconstruction 'arithmetic', we choose equally spaced lattice points $a_n$ between the value $a_N$ and $a_0=1$. Explicitly, we chose $$a_n = a + \frac{1-a}{N-1}(N-1-n), 0 \leq n \leq N, \qquad (2.2.3)$$

with $a=0.2$. Hence, the last point where $\sigma$ is updated is $a_{N-1}=a$. The reconstruction of $\sigma$ was obtained by applying the layer stripping algorithm to data with random error added to each Fourier mode $w_n$. The noise was assumed to be independent at each channel, normally distributed and with variance 0.001 times the value of the largest of the data points $w_n$. We see that with even this low noise level, the reconstructed conductivity deviates greatly from the true profile.

To compare the choice (2.2.3) to differently chosen lattice points, we produced another reconstruction with exactly the same data set but we used formula (2.2.2) as a guideline for fixing the lattice points and chose $$a_n = a_N^{1/(N+1-n)}, 1 \leq n \leq N.$$

To obtain figures comparable to those with equally spaced mesh, we picked $$a_{N-1} = a, \qquad (2.2.4)$$

i.e., $$a_n = a^{2/(N+1-n)}, 1 \leq n \leq N, \qquad (2.2.5)$$

with $a=0.2$.

The reconstruction is much more stable than with the previous choice. Hence, we discard the arithmetic choice and proceed with the geometric one.

For the next comparison of different choices of the lattice points, we assumed that in formula (2.2.1), the noise levels $\epsilon_n$ are equal for all channels, $\epsilon_n=\epsilon$, which corresponds best to the situation. The approximate identity $$r_n = \left(\frac{|n|\sigma_0\epsilon}{1+|n|\sigma_0\epsilon}\right)^{1/2|n|} \approx (|n|\sigma_0\epsilon)^{1/2|n|}$$

then suggests that one should use the choice $$a_n = ((N+1-n)a_N)^{1/(N+1-n)}.$$

In order that this choice satisfy (2.2.4), we chose $a_N=a^2/2$, and hence $$a_n = \left(\frac{N+1-n}{2}a^2\right)^{1/(N+1-n)}, 1 \leq n \leq N. \qquad (2.2.6)$$

Again, the reconstruction is made with the same data as in the previous cases and the outcome is 'corrected'. For comparison, reconstruction was made with the previous choice in the same picture.

In this example, the new choice (2.2.6) seems to outstand almost as much as did the 'geometric' choice against the 'arithmetic' one.

To get better idea of the tolerance of difference choices additive noise, we ran the reconstruction algorithm with different noise levels and computed the average $L^2$ and $L^\infty$ norms of the reconstruction errors with a large number of data samples containing independent additive noise. The outcomes of these runs indicate that each improvement in the choice of lattice points improved the noise tolerance of the method almost by a decade. Thus, we conclude that the formula (2.2.6) is the best of the three.

In all of the succeeding reconstructions, the rule (2.2.6) is thus retained, and we indicate only the size of $a$, henceforth referred to as 'the radius of the smallest detectable object'.

Next, we want to test the sensibility of the algorithm choice of the steplength $\Delta$ appearing in Step 3 to solve the Riccati equation by Euler's method. For the reconstructions we started with data containing no noise other than that due to the numerical round-off errors. The true conductivity profile was plotted, too. Starting with this data, we made two reconstructions that represent in a sense the two external cases:

First, we chose the step $\Delta_n$ be the same as the width of the corresponding ring. Thus, in the propagation step 3, we make just one big leap from the outer boundary of $\Omega_n$ to the inner one. To obtain the other extreme where the stepsize gets infinitely small, we solved the Riccati equation exactly by using the assumption that $\sigma$ is constant in the ring and applied formula (1.2.6).

These two reconstructions seem to suggest that decreasing the stepsize in the propagation procedure improves the dynamical range of the reconstruction. A larger stepsize can thus be seen as one possible regularization parameter. On the other hand, if wider dynamical range is desired, it may be desirable to replace the Euler method by some higher order schemes.

It is maybe not surprising to find out that the use of a first order method in the propagation step yields a first order reconstruction method, i.e., doubling the stepsize doubles the $L^2$ deviation of the reconstruction from that obtained by an 'exact' propagation.

The previous examples give already some idea of the robustness of the algorithm. To get a better idea of how the reconstruction, the radius of the smallest detectable object $\alpha$ and the noise level of the data are interrelated, we made the following test. We chose the same rotationally invariant conductivity profile and computed the corresponding matrix elements of W. From this data, we produced a sample of 20 data sets by adding independent normally distributed zero mean random noise vectors with variance 0.001. With each of these 20 data vectors, we then ran the reconstruction program with different choices of $\alpha$ in formula (2.2.6). For each value of $\alpha$, we then computed the mean of these reconstructions, and the mean square deviation of the reconstructions from this mean profile.

We see that the bigger we choose $\alpha$, the less the reconstruction deviates from the expected value. To get an idea of the deviation of the reconstructed profiles, we have plotted the 20 reconstructions when $\alpha = 1.4$

What is claimed is:

1. A method of creating an impedance image of a volume of a body, the volume having a selected number of finite dimensions and the volume varying in at least one of conductivity and permittivity characteristics in all of the selected number of finite dimensions, the body having an outer boundary, the method comprising:
   (a) applying a set of current or voltage patterns to the outer boundary to create actual resulting and respective voltage or current patterns at the outer boundary;
   (b) measuring the actual resulting and respective voltage or current patterns at the outer boundary;
   (c) finding at least one of the conductivity and permittivity characteristics at the outer boundary of the body based only on the resulting patterns and information about the outer boundary;
   (d) calculating synthesized resulting and respective voltage or current patterns for a first inner boundary which is at a selected incremental distance inward of the outer boundary as a function of the measuring and finding steps only;
   (e) finding said characteristics at the inner boundary of the body based on the calculated resulting patterns;
   (f) calculating synthesized and respective voltage or current patterns for a second inner boundary of the body which is at the selected incremental distance inward of the first inner boundary, as a function of the calculating step (d) and the finding step (e);
   (g) repeating steps (e) and (f) for additional inner boundaries until the selected incremental distance inward reaches a selected depth in the body, the repeated calculating of step (f) also being a function of at least one previous step (f); and
   (h) using said characteristics obtained to form an image of the body from the outer boundary to the selected depth.

2. A method according to claim 1 including a regularization method.

3. A method according to claim 2 including regularizing by expressing the resulting patterns as discrete trigonometric functions having a plurality of modes each containing some information for a particular boundary, determining which mode for each calculated pattern contains least information for a particular boundary, and dropping the mode containing least information.

4. A method according to claim 1, wherein the selected depth is the center of the body.

5. A method according to claim 1 including applying the set of current or voltage patterns through a plurality of electrodes on the outer boundary of the body and measuring the actual resulting and respective voltage or current patterns at the electrodes.

6. A method of creating an impedance image of a volume of a body, the volume having a selected number of finite dimensions and the volume having at least some of conductivity and permittivity characteristics, the body having an outer boundary, the method comprising:
   (a) applying a set of current or voltage patterns to the outer boundary to create actual resulting and respective voltage or current patterns at the outer boundary;
   (b) measuring the actual resulting and respective voltage or current patterns at the outer boundary;
   (c) finding at least one of the conductivity and permittivity characteristics at the outer boundary of the body based only on the resulting patterns and information about the outer boundary;
   (d) calculating synthesized resulting and respective voltage or current patterns for a first inner boundary which is at a selected incremental distance inward of the outer boundary as a function of the measuring and finding steps only;
   (e) finding said characteristics at the inner boundary of the body based on the calculated resulting patterns;
   (f) calculating synthesized and respective voltage or current patterns for a second inner boundary of the body which is at the selected incremental distance inward of the first inner boundary, as a function of the calculating step (d) and the finding step (e);
   (g) repeating steps (e) and (f) for additional inner boundaries until the selected incremental distance inward reaches a selected depth in the body, the repeated calculating of step (f) also being a function of at least one previous step (f); and
   (h) using said characteristics obtained to form an image of the body from the outer boundary to the selected depth.

* * * * *